(12) United States Patent
Piccicuto et al.

(10) Patent No.: US 11,074,534 B2
(45) Date of Patent: Jul. 27, 2021

(54) METHOD OF DETERMINING A MICROBIOLOGICAL RISK LEVEL IN A FOOD BATCH

(71) Applicant: Tetra Laval Holdings & Finance S.A., Pully (CH)

(72) Inventors: Luca Piccicuto, Mappano (IT); Pietro Tarantino, Modena (IT)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days.

(21) Appl. No.: 16/762,297

(22) PCT Filed: Oct. 23, 2018

(86) PCT No.: PCT/EP2018/078979
§ 371 (c)(1),
(2) Date: May 7, 2020

(87) PCT Pub. No.: WO2019/091773
PCT Pub. Date: May 16, 2019

(65) Prior Publication Data
US 2020/0380448 A1    Dec. 3, 2020

(30) Foreign Application Priority Data

Nov. 8, 2017 (EP) ..................... 17200624

(51) Int. Cl.
*G06Q 10/06* (2012.01)
*G06F 17/10* (2006.01)
(Continued)

(52) U.S. Cl.
CPC ....... *G06Q 10/06395* (2013.01); *G06F 17/16* (2013.01); *G06N 7/005* (2013.01); *G06Q 10/087* (2013.01)

(58) Field of Classification Search
USPC ........................................ 708/441
See application file for complete search history.

(56) References Cited

U.S. PATENT DOCUMENTS

| | | | |
|---|---|---|---|
| 5,402,363 A | 3/1995 | Siebart | |
| 2015/0020199 A1* | 1/2015 | Neil | H04L 63/1433 726/23 |

(Continued)

FOREIGN PATENT DOCUMENTS

| | | |
|---|---|---|
| CN | 102768711 A | 11/2012 |
| JP | 2001 209797 A | 8/2001 |

OTHER PUBLICATIONS

Ensor et al., Point Source Influence on Observed Extreme Pollution Level in a Monitoring Network, 2014, Elsevier, Atmospheric Environment, 1-8 (Year: 2014).*

(Continued)

*Primary Examiner* — Timothy Padot
*Assistant Examiner* — Allison M Robinson
(74) *Attorney, Agent, or Firm* — Knobbe Martens Olson & Bear LLP

(57) ABSTRACT

A method of determining a microbiological risk level in food, comprising determining zero-inflated binomial (ZIB) distribution parameters ($\pi$, p); i) determining cumulative relative frequencies ($f_0$, $f_1$, $f_2$, ..., $f_x$) for a number of occurrences (0, 1, 2, x) of defective samples; ii) calculating a vector of a sub-set of zero-inflation parameters ($\pi$) of k+1 elements according to; o/o=[0, 1* $f_0$/k, 2*$f_0$/k, k*$f_0$/k]; iii) calculating a vector of a sub-set of first parameters ($\beta$) based on the sub-set of zero-inflation parameter ($\pi$); iv) for the vector pairs (p, $\pi$) in the sub-set of first parameters and the sub-set of zero-inflation parameters, determining a square error between said cumulative relative frequencies and cumulative theoretical probabilities $P_x$ of having ≤x occurrences over N samples for a ZIB distribution; v) determining (Continued)

the zero-inflation parameter $_{\mu}$) and the first parameter (p) as the vector pair providing the least square error.

18 Claims, 5 Drawing Sheets

(51) Int. Cl.
  *G06N 7/00* (2006.01)
  *G06Q 10/08* (2012.01)
  *G06F 17/16* (2006.01)

(56) References Cited

U.S. PATENT DOCUMENTS

2017/0003300 A1* 1/2017 Bowler .............. G01N 33/6893
2019/0073445 A1* 3/2019 Shen ...................... G16B 40/00

OTHER PUBLICATIONS

Duarte et al., Impact of Microbial Count Distributions on Human Health Risk Estimates, 2015, Elsevier, International Journel of Food Microbiology, 48-57 (Year: 2015).*
International Search Report; PCT/EP2018/078979; dated Jan. 30, 2019; 2 pages.
Written Opinion of the International Searching Authority; PCT/EP2018/078979; dated Jan. 30, 2019; 5 pages.
Extended European Search Report; EP18201966.1; dated Apr. 9, 2019; 5 pages.

* cited by examiner

METHOD OF DETERMINING A MICROBIOLOGICAL RISK LEVEL IN A FOOD BATCH

TECHNICAL FIELD

The present invention relates to the field of statistical quality control for aseptic packaging. More particularly, the present invention relates to a method of determining a microbiological risk level in a food batch, a related computer program product and a system for determining a microbiological risk level.

BACKGROUND

Quality monitoring systems are used in all fields of industries to assess and optimize production performance. In the food packaging industry the performance of a machine which fills shelf-stable food packages is called aseptic performance and is defined by the long-run ratio between the number of not commercially sterile packages and the total number of packages filled by the machine. Sampling of the aseptic data is done by retrieving microbiological sampling data over periods of time. E.g. when a filling machine is installed at a customer site, a validation test is done to prove it can provide an aseptic packaging quality level in compliance with customer's requests. A filling machine passes the validation test when it shows to be able of producing a certain number of packages maintaining the unsterile packages percentage under a certain threshold. Food package inspection is typically conducted according to a sampling plan in order to be able to identify problems in the machine that could compromise the packages sterility. It is desirable to develop efficient tools and procedures for the quality control in this regard, since the sampling and inspection activities are disruptive and costly for the production. Since filling machines provide very high quality, aseptic production can be considered a high yield process, i.e. the defect rate is very low. This also put particular demands on the modelling of the process. An issue with previous quality control tools to is thus to model the aseptic quality data with sufficient accuracy in the fitted statistical distributions. A problem is thus how to implement a reliable quality control tool and strategy with a minimum impact on the production.

Hence, an improved method of determining a microbiological risk level in a food batch would be advantageous and in particular allowing for avoiding more of the above-mentioned problems and compromises, including providing for improved modelling of the aseptic quality data, improved accuracy of forecasting and risk evaluation analyses, and improved production inspection tools.

SUMMARY

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect a method of determining a microbiological risk level in a food batch of a plurality of sets (s) of samples (N) is provided. The method comprises obtaining microbiological sampling data from the plurality of sets of samples, determining a zero-inflated binomial (ZIB) distribution of the microbiological sampling data comprising determining ZIB distribution parameters ($\pi$, p) comprising a first parameter (p) and a zero-inflation parameter ($\pi$), wherein determining the ZIB distribution parameters comprises; i) determining cumulative relative frequencies ($f_0$, $f_1$, $f_2$, ..., $f_x$) for a number of occurrences (0, 1, 2, ..., x) of defective samples in respective sets of samples, wherein the cumulative relative frequency of non-defective samples is determined as $f_0$; ii) calculating a vector of a sub-set of zero-inflation parameters ($\underline{\pi}$) of k+1 elements according to; $\underline{\pi}=[0, 1*f_0/k, 2*f_0/k, ..., k*f_0/k]$; iii) calculating a vector of a sub-set of first parameters ($\underline{p}$) based on the sub-set of zero-inflation parameter ($\underline{\pi}$) according to;

$$\underline{p} = 1 - \sqrt[N]{\frac{f_0 - \pi}{1 - \pi}}$$

iv) for the vector pairs ($\underline{p}$, $\underline{\pi}$) in the sub-set of first parameters and the sub-set of zero-inflation parameters, determining a square error between said cumulative relative frequencies and cumulative theoretical probabilities $P_x$ of having ≤x occurrences over N samples for a ZIB distribution with the respective vector pairs ($\underline{p}$, $\underline{\pi}$) as parameters; v) determining the zero-inflation parameter ($\pi$) and the first parameter (p) as the vector pair providing the least square error. The method comprises determining the ZIB distribution based on the first parameter (p) and the zero-inflation parameter ($\pi$), and detecting a deviation from the ZIB distribution for a subsequent food batch of samples for determining of the microbiological risk level based on said deviation.

According to a second aspect a computer program product comprising instructions which, when the program is executed by a computer, cause the computer to carry out the steps of the method according to the first aspect.

According to a third aspect a system for determining a microbiological risk level in a food batch of a plurality of sets (s) of samples (N) is provided. The system comprises a sampling device configured to obtain microbiological sampling data from the plurality of sets of samples, a processor configured to determine a zero-inflated binomial (ZIB) distribution of the microbiological sampling data by being configured to determine ZIB distribution parameters ($\pi$, p) comprising a first parameter (p) and a zero-inflation parameter ($\pi$). The processor is configured to; i) determine cumulative relative frequencies ($f_0$, $f_1$, $f_2$, ..., $f_x$) for a number of occurrences (0, 1, 2, ..., x) of defective samples in respective sets of samples, wherein the cumulative relative frequency of non-defective samples is determined as $f_0$; ii) calculate a vector of a sub-set of zero-inflation parameters ($\underline{\pi}$) of k+1 elements according to; $\underline{\pi}=[0, 1*f_0/k, 2*f_0/k, ..., k*f_0/k]$; iii) calculate a vector of a sub-set of first parameters ($\underline{p}$) based on the sub-set of zero-inflation parameter ($\underline{\pi}$) according to;

$$\underline{p} = 1 - \sqrt[N]{\frac{f_0 - \pi}{1 - \pi}}$$

iv) for the vector pairs ($\underline{p}$, $\underline{\pi}$) in the sub-set of first parameters and the sub-set of zero-inflation parameters, determine a square error between said cumulative relative frequencies and cumulative theoretical probabilities $P_x$ of having ≤x occurrences over N samples for a ZIB distribution with the respective vector pairs ($\underline{p}$, $\underline{\pi}$) as parameters; v) determine the zero-inflation parameter ($\pi$) and the first parameter (p) as the vector pair providing the least square error. The processor is configured to determine the ZIB distribution based on the first parameter (p) and the zero-inflation parameter (π), and detect a deviation from the ZIB distribution for a subsequent food batch of samples to determine the microbiological risk level based on said deviation.

Further examples of the invention are defined in the dependent claims, wherein features for the second and third aspects of the disclosure are as for the first aspect mutatis mutandis.

Some examples of the disclosure provide for improved modelling of aseptic quality data.

Some examples of the disclosure provide for improved accuracy of forecasting and risk evaluation analyses.

Some examples of the disclosure provide for improved production inspection tools.

Some examples of the disclosure provide for improved estimation of parameters of a zero-inflated binomial distribution for a more accurate fit to aseptic quality data.

Some examples of the disclosure provide for facilitated and less time-consuming identification of faulty elements or functionalities in a filling machine.

Some examples of the disclosure provide for a more efficient use of resources to identify erroneous behavior in a machine.

Some examples of the disclosure provide for a more predictable and efficient maintenance schedule of a machine component.

Some examples of the disclosure provide for a more efficient method of evaluating the quality of a machine.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which.

DETAILED DESCRIPTION

Figure 1A:
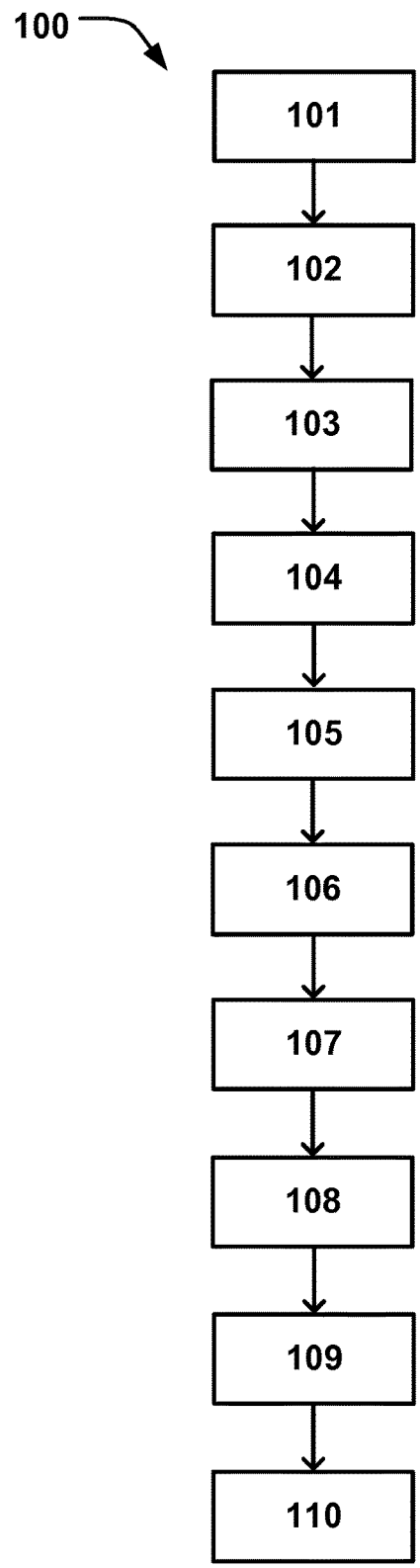
FIG. 1a is a flowchart of a method of determining a microbiological risk level in a food batch, according to examples of the disclosure.

Specific examples of the invention will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art.

The terminology used in the detailed description of the examples illustrated in the accompanying drawings is not intended to be limiting of the invention. In the drawings, like numbers refer to like elements.

FIG. 1a illustrates a flow chart of a method 100 of determining a microbiological risk level in a food batch. The order in which the steps of the method 100 are described and illustrated should not be construed as limiting and it is conceivable that the steps can be performed in varying order. A method 100 of determining a microbiological risk level in a food batch of a plurality of sets (s) of samples (N) is thus provided. Each set (s) may thus comprise N samples. The method 100 comprises obtaining 101 microbiological sampling data from the plurality of sets (s) of samples, and determining 102 a zero-inflated binomial (ZIB) distribution of the microbiological sampling data, which comprises determining 103 ZIB distribution parameters (π, p). The ZIB distribution parameters comprise a first parameter (p) and a zero-inflation parameter (π). Determining the ZIB distribution parameters comprises; i) determining 104 cumulative relative frequencies $(f_0, f_1, f_2, \ldots, f_x)$ for a number of occurrences $(0, 1, 2, \ldots, x)$ of defective samples in respective sets of samples. The cumulative relative frequency of non-defective samples is determined as $f_0$. For example, if there are 13 sets each having one occurrence of a defect sample, then the relative frequency $f'_1$ is given by 13 divided by the total number of sets, and so on, and the cumulative relative frequencies are subsequently given by summing the respective relative frequencies; $f_0=f'_0$, $f_1=f'_0+f'_1, \ldots, f_x=f'_0+f'_1+\ldots+f'_x$. I.e. the cumulative relative frequencies $f_x$ may be determined by the number of sets (s') each having an occurrence ≤x divided by total number of sets (s).

The method 100 comprises ii) calculating 105 a vector of a sub-set of zero-inflation parameters ($\underline{\pi}$) of k+1 elements according to; $\underline{\pi}=[0, 1*f_0/k, 2*f_0/k, \ldots, k*f_0/k]$, where k is a constant which may be optimized depending on the application. The method 100 comprises iii) calculating 106 a vector of a sub-set of first parameters ($\underline{p}$) based on the sub-set of zero-inflation parameter ($\underline{\pi}$) according to;

$$\underline{p} = 1 - \sqrt[N]{\frac{f_0 - \pi}{1 - \pi}}$$

The method 100 further comprises iv) determining 107, for the vector pairs ($\underline{p}, \underline{\pi}$) in the sub-set of first parameters and the sub-set of zero-inflation parameters, a square error between the aforementioned cumulative relative frequencies $(f_0, f_1, f_2, \ldots, f_x)$ and cumulative theoretical probabilities $P_x$ of having ≤x occurrences over N samples for a ZIB distribution with the respective vector pairs ($\underline{p}, \underline{\pi}$) as parameters. Thus, a first vector pair $\underline{p}_1, \underline{\pi}_1$, may be calculated as explained above. Then the cumulative theoretical probability $P_x$ may be determined for the first vector pair $\underline{p}_1, \underline{\pi}_1$, as input parameters to the ZIB distribution. The determined $P_x$ is then used as basis for determining the square error associated with the first vector pair $\underline{p}_1, \underline{\pi}_1$. The method 100 comprises v) determining 108 the zero-inflation parameter (π) and the first parameter (p) as the vector pair providing the least square error. I.e. all vector pairs $\underline{p}, \underline{\pi}$, may be calculated, and the vector pair resulting in a square error having the lowest value is chosen as the input parameters for the ZIB distribution. Thus, the method 100 comprises determining 109 the ZIB distribution based on the first parameter (p) and the zero-inflation parameter (π), providing the least square error, and further, detecting 110 a deviation from the ZIB distribution for a subsequent food batch of samples for determining of the microbiological risk level based on the aforementioned deviation. Determining the first parameter (p) and the zero-inflation parameter (π) for the ZIB distribution based on the square error minimization between the cumulative relative frequencies and the theoretical probabilities $P_x$ provides for a more accurate fitting of the ZIB distribution to the aseptic data, such as the data sampled from a high-yield filling machine 301 for food containers. Hence, an improved modelling of the aseptic data can be achieved. A more reliable assessment of a microbiological risk level can be provided over time as further data is collected during operation of the filling machine and compared to the fitted ZIB distribution, which may be determined for a know in-control state or calibrated state of the filling machine. Issues with previous modelling methods, such as when fitting the data to standardized binomial distributions can thus be avoided. The improved accuracy of the ZIB distribution allows for more efficient production inspection tools and the time spend on assessing risk can be reduced, and the through-put of the production may be increased while maintaining a high confidence interval of an ascertained quality level. Condition monitoring and understanding of machine behavior can also be facilitated, which in turn opens for more efficient methods of evaluating the quality of a machine, identification of erroneous behavior in the machine, and for more predictable and efficient maintenance schedules.

As mentioned, the cumulative relative frequencies $f_x$ may be determined by the number of sets (s') each having an occurrence ≤x divided by total number of sets (s). The square error (sqe) may be determined by; sqe=$(f_0-P_0)^2+ \ldots +(f_M-P_M)^2$, where M is the maximum number of occurrences (x) of a defect in a set (s) of samples, $f_x$ is the cumulative relative frequencies, $P_x$ the cumulative theoretical probabilities, where each $P_x$ is determined for a theoretical ZIB distribution with the sub-set of parameters p, π, as described above. For example, if M=2, then sqe=$(f_0-P_0)^2+(f_1-P_1)^2+(f_2-P_2)^2$.

The cumulative theoretical probabilities $P_x$ may be determined according to:

$$P_0 = P'_0$$
$$P_1 = P'_0 + P'_1$$
$$\ldots$$
$$P_x = P'_0 + P'_1 + \ldots + P'_x$$

where;

$$P'_x = \begin{cases} \pi + (1-\pi)(1-p)^N & \text{if } x = 0 \\ (1-\pi)\binom{N}{x}p^x(1-p)^{N-x} & \text{if } x = 1, 2, \ldots, M \end{cases}$$

For example, given a first vector pair $\underline{p}_1, \underline{\pi}_1$, as candidates of the zero-inflation parameter (π) and the first parameter (p), and M=2, $P'_x$ is determined as;

$$P'_0 = \underline{\pi}_1 + (1-\underline{\pi}_1)(1-\underline{p}_1)^N$$

$$P'_1 = (1-\underline{\pi}_1)\binom{N}{1}\underline{p}_1^1(1-\underline{p}_1)^{N-1}$$

-continued
$$P'_2 = (1-\underline{\pi}_1)\binom{N}{2}\underline{p}_1^2(1-\underline{p}_1)^{N-2}$$

$P_x$ may thus be determined for each vector pair $\underline{p}, \underline{\pi}$, of the sub-sets of ZIB parameters, and used as basis for determining the square error (sqe) as exemplified above. The vector pair resulting in the lowest square error is chosen as the input parameters for the ZIB distribution.

Figure 1B:
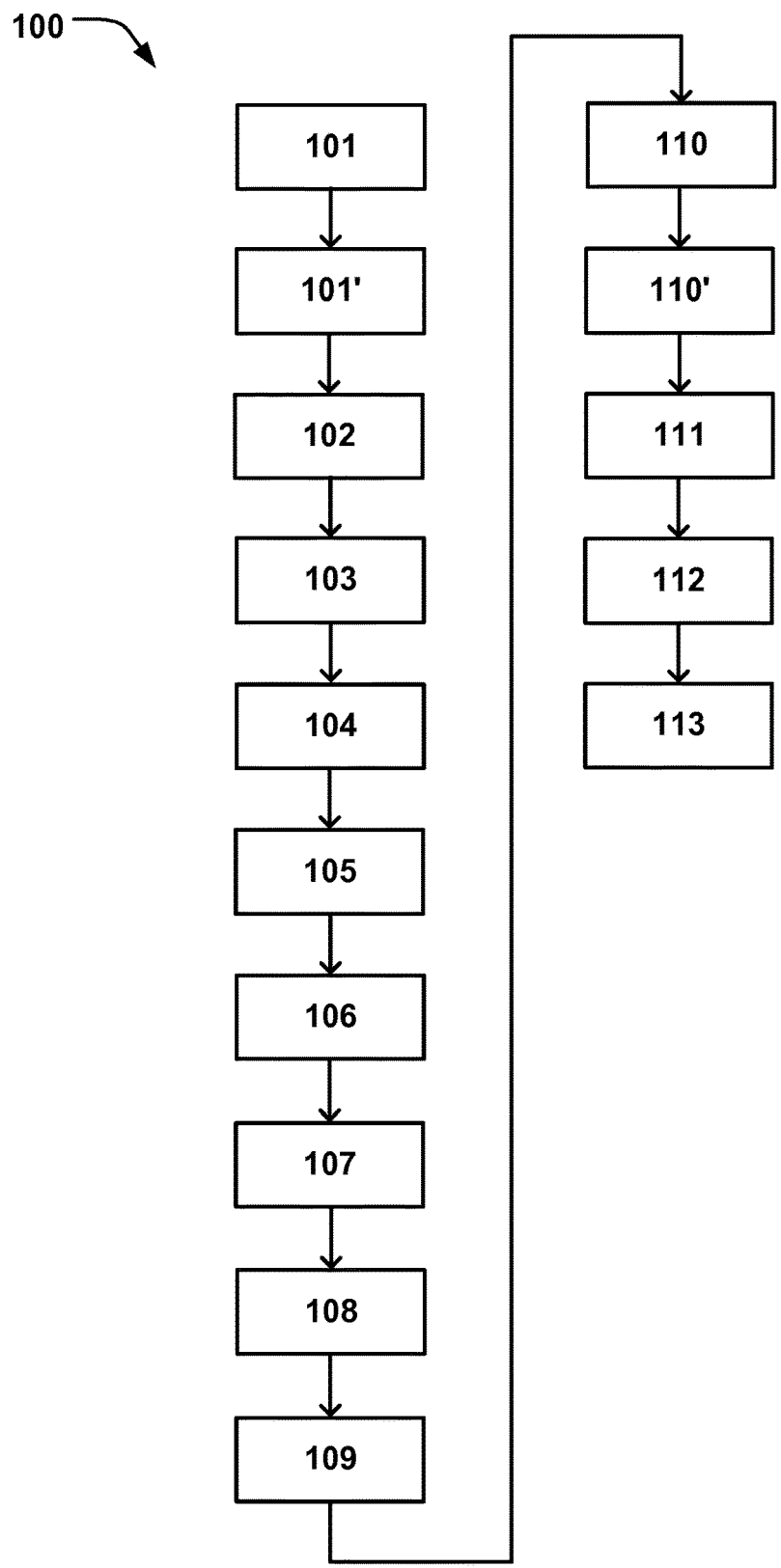
FIG. 1b is a flowchart of a method of determining a microbiological risk level in a food batch, according to examples of the disclosure.

FIG. 1b illustrates a further flow chart of a method 100 of determining a microbiological risk level in a food batch. The order in which the steps of the method 100 are described and illustrated should not be construed as limiting and it is conceivable that the steps can be performed in varying order.

Detecting a deviation from the ZIB distribution for a subsequent food batch of samples may comprise determining 110' a deviation according to a predetermined statistical measure for obtaining the microbiological risk level. Hence, the subsequently obtained aseptic data may be compared to the ZIB distribution, to evaluate if the ZIB distribution still describes the data or if there is a statistically significant deviation. In the latter case, the aseptic data may be indicative of an increased microbiological risk level.

The predetermined statistical measure may comprise a statistical hypothesis measure, such as a chi-square test ($\chi^2$) for determining a confidence value as the microbiological risk level. Other statistical test may also be utilized to evaluate to what extent any subsequent aseptic data fits the initial ZIB distribution. The confidence value of such statistical test can thus be indicative of the microbiological risk level.

The method 100 may comprise providing 111 a set of alert levels according to predetermined thresholds of confidence values. Such thresholds and alert levels may further be incorporated in a quality monitoring tool, such that a user may be alerted of different levels of deviations in the aseptic data as the production line is in operation.

The method 100 may comprise determining 112 respective confidence values for a plurality of subsequent food batches, and tagging 113 the subsequent food batches with respective alert levels associated with the confidence values. This provides for a facilitated quality control where released batches may be tracked via labels or tags associated with the particular confidence values or alert levels determined according to the aforementioned statistical tests.

The method 100 may comprise obtaining 101' microbiological sampling data of the subsequent food batch of samples over a predetermined fixed time interval. Hence, the interval over which the aseptic data is collected may be a window of a predetermined amount of time that may be optimized to the particular application. It is however conceivable that the length time window may be varied continuously depending on the outcome of the ZIB distribution fitting or subsequent deviations from the ZIB distribution. E.g. more significant deviations and lower confidence values may motivate more intermittent controls and shorter sampling times.

A computer program product is provided comprising instructions which, when the program is executed by a computer, cause the computer to carry out the steps of the method 100 as described above with respect to FIG. 1a-b.

Figure 2:
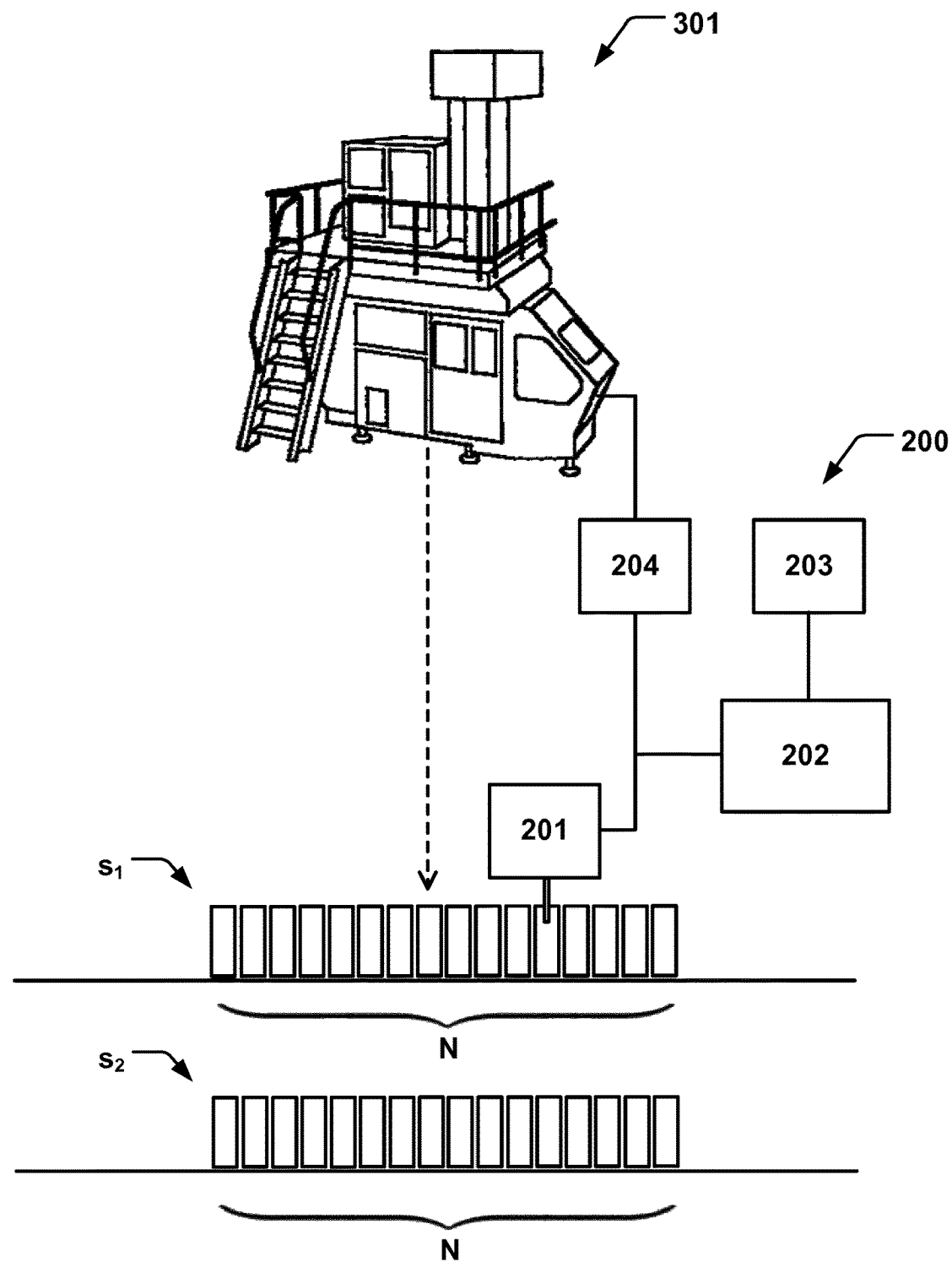
FIG. 2 is a schematic illustration of a system configured for determining a microbiological risk level in a food batch of a plurality of sets (s) of samples (N) in a filling machine, according to examples of the disclosure.

FIG. 2 is a schematic illustration of processor 202 configured to execute the method 100 as described above with respect to FIG. 1a-b in a filling machine 301. A system 200 for determining a microbiological risk level in a food batch of a plurality of sets (s) of samples (N) in a filling machine 301 is thus provided. The system 200 comprises a sampling device 201 configured to obtain 101 microbiological sampling data from the plurality of sets of samples (exemplified as sets $s_1$ and $s_2$ in FIG. 2, where the samples are taken from respective packaging containers in a filling machine 301 by the sampling device 201), and a processor 202 configured to determine 102 a zero-inflated binomial (ZIB) distribution of the microbiological sampling data by being configured to determine 103 ZIB distribution parameters (π, p) comprising a first parameter (p) and a zero-inflation parameter (π). The processor 202 is configured to; i) determine 104 cumulative relative frequencies ($f_0$, $f_1$, $f_2$, . . . , $f_x$) for a number of occurrences (0, 1, 2, . . . , x) of defective samples in respective sets of samples, wherein the cumulative relative frequency of non-defective samples is determined as $f_0$; ii) calculate 105 a vector of a sub-set of zero-inflation parameters (π̱) of k+1 elements according to; π̱=[0, 1*$f_0$/k, 2*$f_0$/k, . . . , k*$f_0$/k]; iii) calculate 106 a vector of a sub-set of first parameters (p̱) based on the sub-set of zero-inflation parameter (π̱) according to;

$$p = 1 - \sqrt[N]{\frac{f_0 - \pi}{1 - \pi}}$$

The processor 202 is configured to iv) determine 107, for the vector pairs (p̱, π̱) in the sub-set of first parameters and the sub-set of zero-inflation parameters, a square error between said cumulative relative frequencies and cumulative theoretical probabilities $P_x$ of having ≤x occurrences over N samples for a ZIB distribution with the respective vector pairs (p̱, π̱) as parameters. The processor 202 is configured to v) determine 108 the zero-inflation parameter (π) and the first parameter (p) as the vector pair providing the least square error. The processor 202 is configured to determine 109 the ZIB distribution based on the first parameter (p) and the zero-inflation parameter (π), and detect 110 a deviation from the ZIB distribution for a subsequent food batch of samples for determine of the microbiological risk level based on said deviation. The system 200 thus provides for the advantageous benefits as described above in relation to the method 100 and FIGS. 1a-b.

The processor 202 may be configured to determine the cumulative relative frequencies $f_x$ according to; $f_x$=the number of sets (s') each having an occurrence ≤x/the total number of sets (s). The processor 202 may be configured to determine the square error (sqe) according to; sqe=$(f_0-P_0)^2$+ . . . +$(f_M-P_M)^2$, where M is the maximum number of occurrences (x).

The processor 202 may be configured to determine the cumulative theoretical probabilities $P_x$ according to:

$$P_0 = P'_0$$
$$P_1 = P'_0 + P'_1$$
$$\ldots$$
$$P_x = P'_0 + P'_1 + \ldots + P'_x$$

where;

$$P'_x = \begin{cases} \pi + (1-\pi)(1-p)^N & \text{if } x = 0 \\ (1-\pi)\binom{N}{x}p^x(1-p)^{N-x} & \text{if } x = 1, 2, \ldots, M \end{cases}$$

Figure 3A:
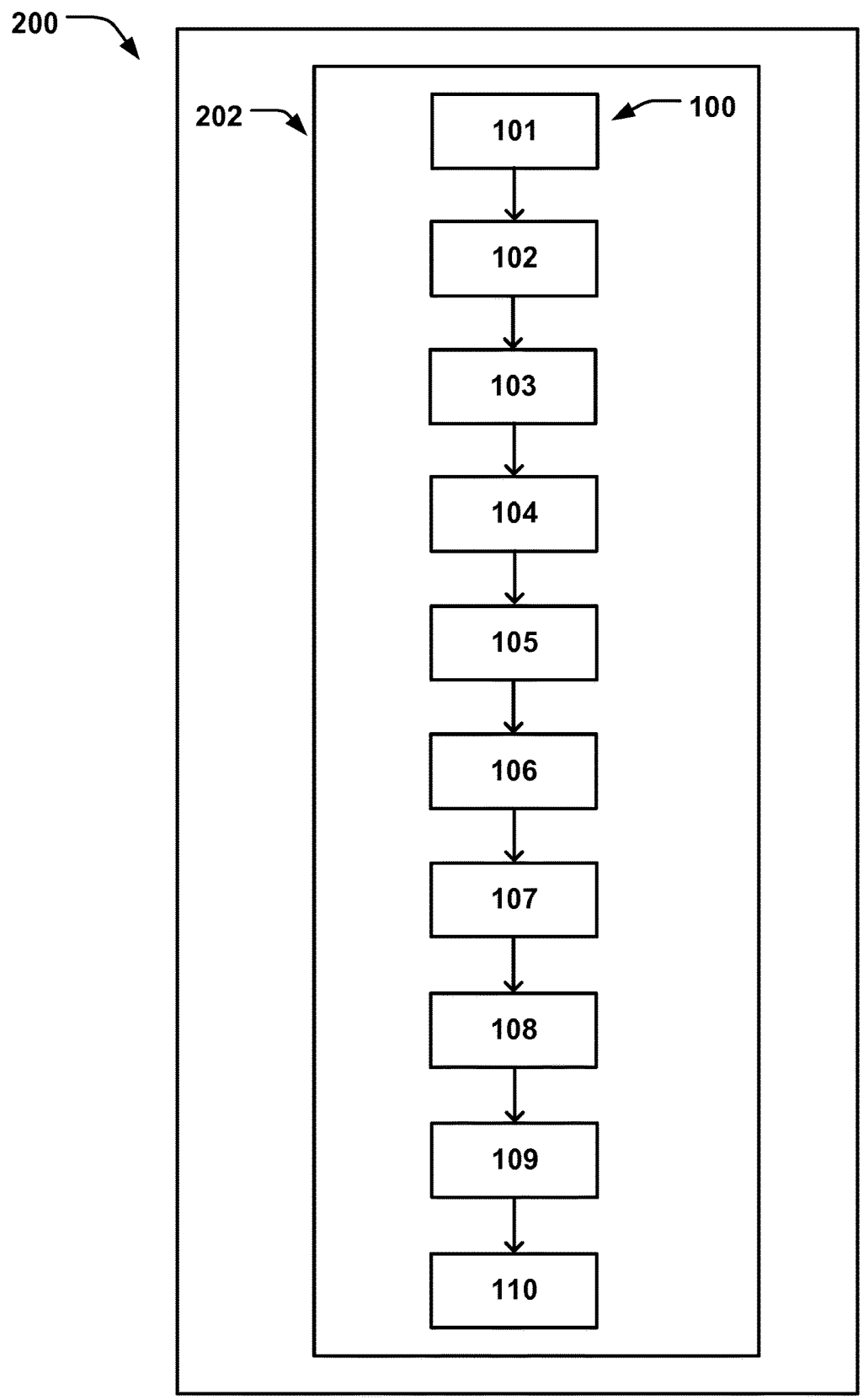
FIGS. 3a-b are schematic illustrations of a system configured for determining a microbiological risk level in a food batch of a plurality of sets (s) of samples (N) in a filling machine, according to examples of the disclosure.
Figure 3B:
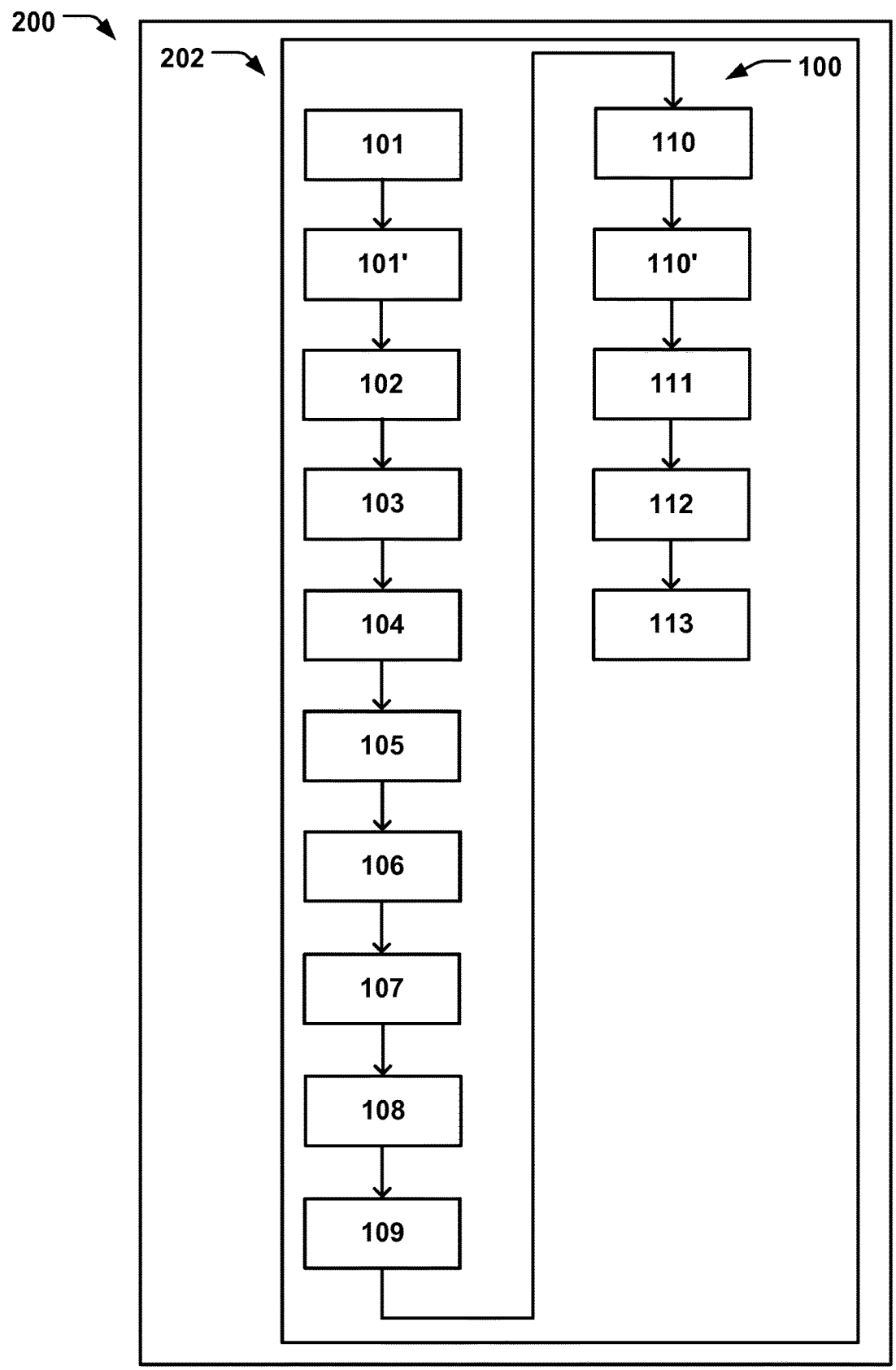

The method 100 can be implemented by the system 200 described herein. In some embodiments, the method 100 is implemented by the system 200 using the processor 202 and sampling device 201. FIGS. 3a-b are further illustrations of the processor 202 of the system 200 being configured to execute the method 100 as described in relation to FIGS. 1a-b, respectively.

The processor 202 may be configured to determine 110' a confidence value from a statistical hypothesis measure, such as a chi-square test, of said deviation to determine the microbiological risk level, and to determine 111 a set of alert levels associated with predetermined thresholds of confidence values. The system may comprise a display 203 configured to display the alert levels as a graphical or numerical representation on the display 203 to alert a user of the microbiological risk level. The system 200 may further comprise a control unit 204 in communication with the processor 202. The control unit may be configured to communicate with a filling machine 301 to control the filling machine 301 in dependence on the mentioned microbiological sampling data or alert level. The control unit 204 may send control instructions to the filling machine 301 to e.g. stop the filling machine 301 if an alert level associated with a certain confidence value threshold is reached, i.e. if the microbiological risk level is too high. The present invention has been described above with reference to specific examples. However, other examples than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A method of determining a microbiological risk level in a food batch of a plurality of sets of samples, the method comprising:
   by a sampling device of a system for determining the microbiological risk level in the food batch, obtaining microbiological sampling data from the plurality of sets of samples that are taken from a food packaging machine,
   by a processor of the system for determining the microbiological risk level in the food batch, determining a zero-inflated binomial (ZIB) distribution of the microbiological sampling data by:
      determining ZIB distribution parameters (π, p) comprising a first parameter (p) and a zero-inflation parameter (π), wherein determining the ZIB distribution parameters comprises:
      determining cumulative relative frequencies ($f_0$, $f_1$, $f_2$, . . . , $f_x$) for a number of occurrences (0, 1, 2, . . . , x) of defective samples in respective sets of samples, wherein the cumulative relative frequency of non-defective samples is determined as $f_0$,
      calculating a vector of a sub-set of zero-inflation parameters (π) of k+1 elements according to: π=[0, 1*f0/k, 2*f0/k, . . . , k*f0/k], calculating a vector of a sub-set of first parameters ($\pi$) based on the sub-set of zero-inflation parameter ($\pi$) according to:

$$\underline{p} = 1 - \sqrt[N]{\frac{f_0 - \pi}{1 - \pi}}$$

for the vector pair (p, $\pi$) in the sub-set of first parameters and the sub-set of zero-inflation parameters, determining a square error between said cumulative relative frequencies and cumulative theoretical probabilities Px of having ≤x occurrences over N samples for a ZIB distribution with the respective vector pair (p, $\pi$) as parameters, and determining the zero-inflation parameter ($\pi$) and the first parameter (p) as the vector pair providing the least square error, by the processor, determining the ZIB distribution based on the first parameter (p) and the zero-inflation parameter ($\pi$), by the processor, detecting a deviation from the ZIB distribution for a subsequent food batch of samples for determining the microbiological risk level based on said deviation, and by the processor, sending a control instruction to the food packaging machine to control operation of the food packaging machine responsive to the microbiological risk level.

2. The method according to claim 1, wherein the cumulative relative frequencies $f_x$ is determined by: $f_x$=number of sets each having an occurrence ≤x /total number of sets.

3. The method according to claim 1, wherein the square error (sqe) is determined by: sqe=$(f_0-P_0)^2 + \ldots +(f_M-P_M)^2$, where M is the maximum number of occurrences (x).

4. The method according to claim 3, wherein the cumulative theoretical probabilities $P_x$ are determined according to:

$$P_0 = P'_0$$
$$P_1 = P'_0 + P'_1$$
$$\ldots$$
$$P_x = P'_0 + P'_1 + \ldots + P'_x$$

where;

$$P'_x = \begin{cases} \pi + (1-\pi)(1-\underline{p})^N & \text{if } x = 0 \\ (1-\pi)\binom{N}{x}\underline{p}^x(1-\underline{p})^{N-x} & \text{if } x = 1, 2, \ldots, M \end{cases}$$

5. The method according to claim 1, wherein detecting a deviation from the ZIB distribution for a subsequent food batch of samples comprises determining a deviation according to a predetermined statistical measure for obtaining said microbiological risk level.

6. The method according to claim 5, wherein the predetermined statistical measure comprises a statistical hypothesis measure, such as a chi-square test, for determining a confidence value as the microbiological risk level.

7. The method according to claim 6, comprising, by the processor, determining a set of alert levels associated with predetermined thresholds of confidence values.

8. The method according to claim 7, comprising, by the processor, determining respective confidence values for a plurality of subsequent food batches, and tagging the subsequent food batches with respective alert levels associated with the confidence values.

9. The method according to claim 1, comprising obtaining, by the sampling device, microbiological sampling data of the subsequent food batch of samples over a predetermined fixed time interval.

10. A non-transitory storage medium storing instructions which, when executed by a processor of a system for determining a microbiological risk level in a food batch of a plurality of sets of samples, cause the processor to carry out a method comprising:

obtaining microbiological sampling data from a sampling device of the system, wherein the sampling device obtains the microbiological sampling data from the plurality of sets of samples that are taken from a food packaging machine, determining a zero-inflated binomial (ZIB) distribution of the microbiological sampling data by:

determining ZIB distribution parameters ($\pi$, p) comprising a first parameter (p) and a zero-inflation parameter ($\pi$), wherein determining the ZIB distribution parameters comprises:

determining cumulative relative frequencies ($f_0$, $f_1$, $f_2$, ..., $f_x$) for a number of occurrences (0, 1, 2, ..., x) of defective samples in respective sets of samples, wherein the cumulative relative frequency of non-defective samples is determined as $f_0$, calculating a vector of a sub-set of zero-inflation parameters ($\pi$) of k+1 elements according to: $\pi$=[0, 1*f0/k, 2*f0/k, ..., k*f0/k], calculating a vector of a sub-set of first parameters (p) based on the sub-set of zero-inflation parameter ($\pi$) according to:

$$\underline{p} = 1 - \sqrt[N]{\frac{f_0 - \pi}{1 - \pi}}$$

for the vector pair (p, $\pi$) in the sub-set of first parameters and the sub-set of zero-inflation parameters, determining a square error between said cumulative relative frequencies and cumulative theoretical probabilities Px of having ≤x occurrences over N samples for a ZIB distribution with the respective vector pair (p, $\pi$) as parameters, and determining the zero-inflation parameter ($\pi$) and the first parameter (p) as the vector pair providing the least square error, determining the ZIB distribution based on the first parameter (p) and the zero-inflation parameter ($\pi$), detecting a deviation from the ZIB distribution for a subsequent food batch of samples for determining the microbiological risk level based on said deviation, and sending a control instruction to the food packaging machine to control operation of the food packaging machine responsive to the microbiological risk level.

11. A system for determining a microbiological risk level in a food batch of a plurality of sets of samples, the system comprising:

a sampling device configured to obtain microbiological sampling data from the plurality of sets of samples that are taken from a food packaging machine, and a processor configured to determine a zero-inflated binomial (ZIB) distribution of the microbiological sampling data by being configured to:
determine ZIB distribution parameters ($\pi$, p) comprising a first parameter (p) and a zero-inflation parameter ($\pi$), wherein the processor is configured to:
determine cumulative relative frequencies ($f_0$, $f_1$, $f_2$, ..., $f_x$) for a number of occurrences (0, 1, 2, ..., x) of defective samples in respective sets of samples, wherein the cumulative relative frequency of non-defective samples is determined as f0,
calculate a vector of a sub-set of zero-inflation parameters ($\pi$) of k+1 elements according to: $\pi$=[0, 1*f0/k, 2*f0/k, ..., k*f0/k],
calculate a vector of a sub-set of first parameters (p) based on the sub-set of zero-inflation parameter ($\pi$) according to:

$$p = 1 - \sqrt[N]{\frac{f_0 - \pi}{1 - \pi}}$$

for the vector pairs (p, $\pi$) in the sub-set of first parameters and the sub-set of zero-inflation parameters, determine a square error between said cumulative relative frequencies and cumulative theoretical probabilities Px of having $\leq$x occurrences over N samples for a ZIB distribution with the respective vector pair (p, $\pi$) as parameters, and
determine the zero-inflation parameter ($\pi$) and the first parameter (p) as the vector pair providing the least square error,
the processor being further configured to:
determine the ZIB distribution based on the first parameter (p) and the zero-inflation parameter ($\pi$),
detect a deviation from the ZIB distribution for a subsequent food batch of samples to determine the microbiological risk level based on said deviation, and
send a control instruction to the food packaging machine to control operation of the food packaging machine responsive to the microbiological risk level.

12. The system according to claim 11, wherein the processor is configured to determine the cumulative relative frequencies $f_x$ according to: $f_x$=the number of sets each having an occurrence $\leq$x / the total number of sets.

13. The system according to claim 11, wherein the processor is configured to determine the square error (sqe) according to: sqe=$(f_0-P_0)^2$+ ... +$(f_M-P_M)^2$, where M is the maximum number of occurrences (x).

14. The system according to claim 13, wherein the processor is configured to determine the cumulative theoretical probabilities $P^c_x$ according to:

$$P_0 = P'_0$$
$$P_1 = P'_0 + P'_1$$
$$...$$
$$P_x = P'_0 + P'_1 + ... + P'_x$$

where;

$$P'_x = \begin{cases} \pi + (1-\pi)(1-\underline{p})^N & \text{if } x = 0 \\ (1-\pi)\binom{N}{x}\underline{p}^x(1-\underline{p})^{N-x} & \text{if } x = 1, 2, ..., M \end{cases}.$$

15. The system according to claim 11, wherein the processor is configured to:
determine a confidence value from a statistical hypothesis measure, such as a chi-square test, of said deviation to determine the microbiological risk level, and
determine a set of alert levels associated with predetermined thresholds of confidence values, the system comprising a display configured to display the alert levels as a graphical or numerical representation on the display to alert a user of the microbiological risk level.

16. The method according to claim 1, wherein sending the control instruction to the food packaging machine causes stopping the operation of the food packaging machine responsive to the microbiological risk level satisfying a threshold.

17. The storage medium according to claim 10, wherein sending the control instruction to the food packaging machine causes stopping the operation of the food packaging machine responsive to the microbiological risk level satisfying a threshold.

18. The system according to claim 11, wherein sending the control instruction to the food packaging machine causes stopping the operation of the food packaging machine responsive to the microbiological risk level satisfying a threshold.

* * * * *

UNITED STATES PATENT AND TRADEMARK OFFICE
CERTIFICATE OF CORRECTION

PATENT NO. : 11,074,534 B2
APPLICATION NO. : 16/762297
DATED : July 27, 2021
INVENTOR(S) : Luca Piccicuto et al.

Page 1 of 2

It is certified that error appears in the above-identified patent and that said Letters Patent is hereby corrected as shown below:

On the Title Page

In Column 2, item (57), ABSTRACT, Line 4, delete "(fo, fi, f2, . . . , $f_x$)" and insert --($f_0$, $f_1$, $f_2$, ... ,$f_x$)--.

In Column 2, item (57), ABSTRACT, Line 6, delete "a sub-set of zero-inflation parameters ($\pi$)" and insert --a sub-set of zero-inflation parameters ($\underline{\pi}$)--.

In Column 2, item (57), ABSTRACT, Line 7, delete "o/o =[0, 1*fo/k, 2*fo/k, k*fo/k];" and insert --$\underline{\pi}$ = [0, 1*$f_0$/k, 2*$f_0$/k, k*$f_0$/k];--.

In Column 2, item (57), ABSTRACT, Line 11, delete "sub¬set" and insert --sub-set--.

On page 2, in Column 1, Line 1, delete "parameter $_{lt)}$" and insert --parameter ($\pi$)--.

On page 2, in Column 1, item (56), Other Publications, Line 2, delete "Journel" and insert --Journal--.

In the Specification

In Column 5, Line 40, delete "p, $\pi$," and insert --$\underline{p}$, $\underline{\pi}$,--.

In Column 6, Line 62, delete "FIG." and insert --FIGS.--.

In Column 6, Line 65, delete "FIG." and insert --FIGS.--.

In the Claims

In Column 8, Lines 65 and 66, Claim 1, delete "a sub-set of zero-inflation parameters ($\pi$)" and insert --a sub-set of zero-inflation parameters ($\underline{\pi}$)--.

Signed and Sealed this
Eighteenth Day of January, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,074,534 B2

In Column 8, Lines 66 and 67, Claim 1, delete "π=[0, 1*f0/k, 2*f0/k, k*f0/k]," and insert --$\underline{\pi}$=[0, 1*$f_0$/k, 2*$f_0$/k, k*$f_0$/k],--.

In Column 9, Line 1, Claim 1, delete "a sub-set of first parameters (π)" and insert --a sub-set of first parameters ($\underline{p}$)--.

In Column 9, Line 14, Claim 1, delete "Px" and insert --$P_x$--.

In Column 9, Line 46 (approx.), Claim 4, delete "where;" and insert --where:--.

In Column 10, Lines 30 and 31 (approx.), Claim 10, delete "a sub-set of zero-inflation parameters (π)" and insert --a sub-set of zero-inflation parameters ($\underline{\pi}$)--.

In Column 10, Lines 31 and 32 (approx.), Claim 1, delete "π=[0, 1*f0/k, 2*f0/k, k*f0/k]," and insert --$\underline{\pi}$=[0, 1*$f_0$/k, 2*$f_0$/k, k*$f_0$/k],--.

In Column 10, Line 33 (approx.), Claim 10, delete "a sub-set of first parameters (p)" and insert --a sub-set of first parameters ($\underline{p}$)--.

In Column 10, Line 34 (approx.), Claim 10, delete "the sub-set of zero-inflation parameters (π)" and insert --the sub-set of zero-inflation parameters ($\underline{\pi}$)--.

In Column 10, Line 47, Claim 10, delete "Px" and insert --$P_x$--.

In Column 11, Line 12 (approx.), Claim 11, delete "f0," and insert --$f_0$,--.

In Column 11, Lines 13 and 14 (approx.), Claim 11, delete "a sub-set of zero-inflation parameters (π)" and insert --a sub-set of zero-inflation parameters ($\underline{\pi}$)--.

In Column 11, Lines 14 and 15 (approx.), Claim 11, delete "π = [0, 1*f0/k, 2*f0/k, k*f0/k]," and insert --$\underline{\pi}$ = [0, 1*$f_0$/k, 2*$f_0$/k, k*$f_0$/k],--.

In Column 11, Line 16 (approx.), Claim 11, delete "a sub-set of first parameters (p)" and insert --a sub-set of first parameters ($\underline{p}$)--.

In Column 11, Line 17 (approx.), Claim 11, delete "the sub-set of zero-inflation parameters (π)" and insert --the sub-set of zero-inflation parameters ($\underline{\pi}$)--.

In Column 11, Line 29, Claim 11, delete "Px" and insert --$P_x$--.

In Column 12, Line 15, Claim 14, delete "where;" and insert --where:--.